(12) United States Patent  (10) Patent No.: US 7,703,335 B2
DiMartino et al.  (45) Date of Patent: Apr. 27, 2010

(54) LOAD TEST SYSTEM

(75) Inventors: John Michael DiMartino, New Bern, NC (US); William David DiMartino, New Bern, NC (US)

(73) Assignee: Tandemloc, Inc., Havelock, NC (US)

( * ) Notice: Subject to any disclaimer, the term of this patent is extended or adjusted under 35 U.S.C. 154(b) by 83 days.

(21) Appl. No.: 12/177,318

(22) Filed: Jul. 22, 2008

(65) Prior Publication Data

US 2009/0064793 A1  Mar. 12, 2009

Related U.S. Application Data

(60) Provisional application No. 60/970,546, filed on Sep. 7, 2007.

(51) Int. Cl.
*G01N 3/02* (2006.01)
(52) U.S. Cl. ........................................ 73/856
(58) Field of Classification Search ........... 73/825, 73/856, 862.393, 862.56
See application file for complete search history.

(56) References Cited

U.S. PATENT DOCUMENTS

| | | | | |
|---|---|---|---|---|
| 3,722,267 A * | 3/1973 | Gordon | ................... | 73/862.56 |
| 3,879,991 A * | 4/1975 | Ristow et al. | ................. | 73/837 |
| 4,509,377 A * | 4/1985 | Mentzell et al. | .......... | 73/862.56 |
| 4,643,031 A * | 2/1987 | Mentzell | .................. | 73/862.56 |
| 6,231,527 B1 * | 5/2001 | Sol | ............................. | 600/595 |
| 6,912,916 B1 * | 7/2005 | Joubert | ........................ | 73/856 |
| 7,591,190 B2 * | 9/2009 | Asher | .......................... | 73/856 |

* cited by examiner

*Primary Examiner*—Lisa M Caputo
*Assistant Examiner*—Freddie Kirkland, III
(74) *Attorney, Agent, or Firm*—Ward and Smith, P.A.

(57) ABSTRACT

A load test system includes a test bed frame which extends horizontally along a first axis and includes two rolling beams moveably mounted securely in the test bed frame for being moved to desired position. The rolling beams have plural attachment locations for attaching a test lift device. A hydraulic power station is located spaced perpendicular from the test bed frame along a second axis and includes a hydraulic cylinder with a line connected to the hydraulic cylinder at one end, which is connectable to a test device at another end for applying a load when the test device is attached to the test bed. Beam members connect the hydraulic power station and the test bed frame to form a rigid structure.

23 Claims, 6 Drawing Sheets

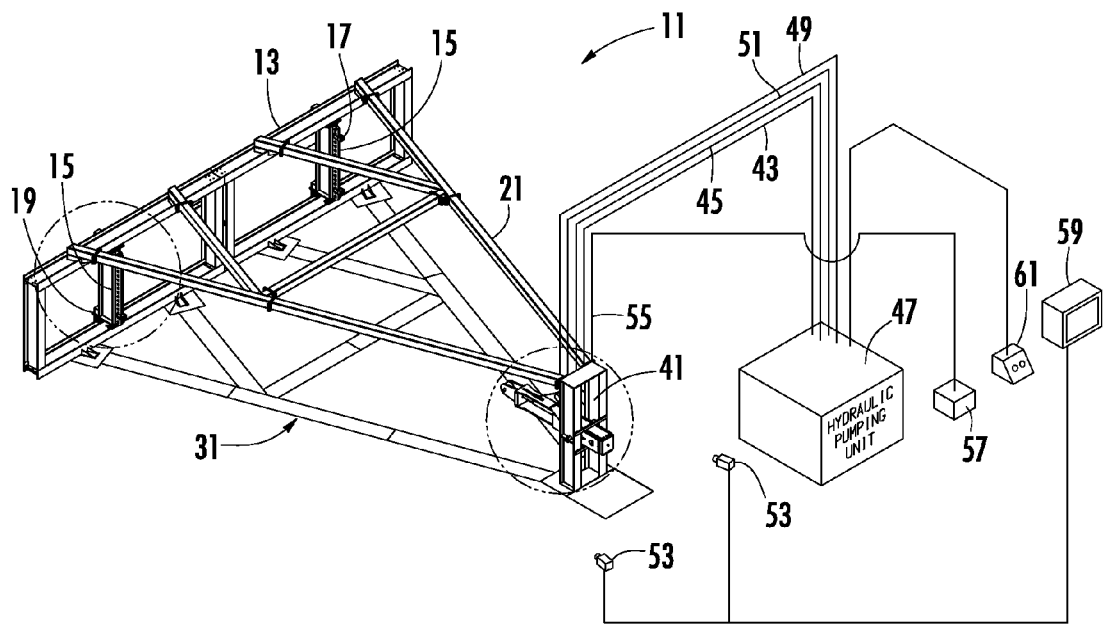
FIG. 1
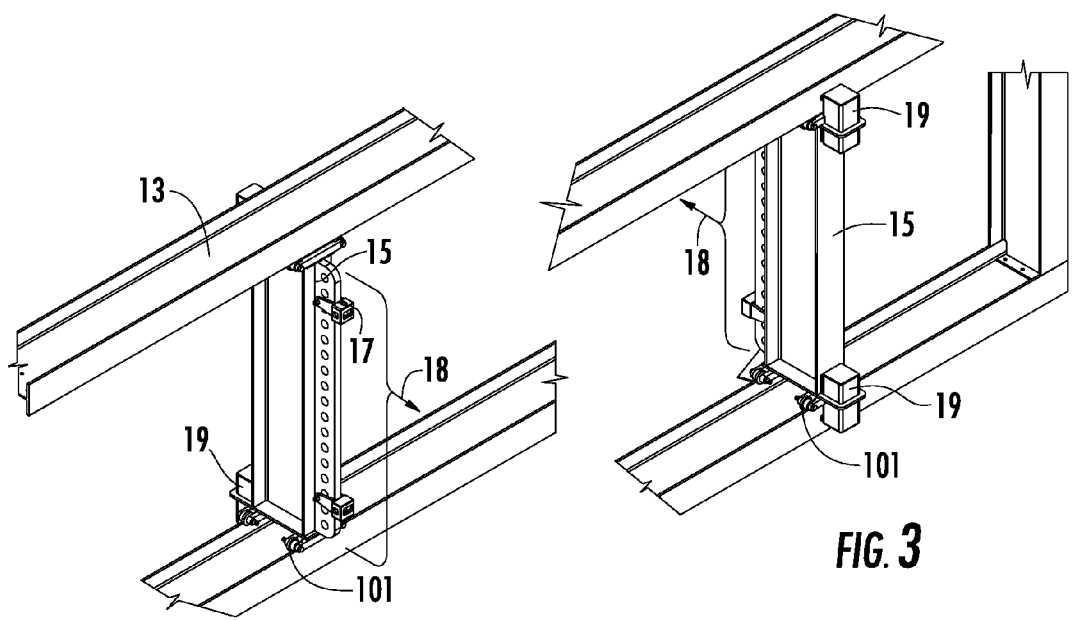
FIG. 2
FIG. 3

LOAD TEST SYSTEM

CROSS REFERENCE TO RELATED APPLICATIONS

This application is related to U.S. Provisional Patent Application Ser. No. 60/970,546 for Load Test System filed Sep. 7, 2007, the disclosure of which is specifically incorporated in its entirety by reference herein. Applicants hereby expressly claim priority to the filing date of Sep. 7, 2007 of Application Ser. No. 60/970,546.

FIELD OF THE INVENTION

This invention relates to a system for load testing devices such as for use with "below-the-hook lifting devices." More particularly, the invention relates to such a test system which provides a standardized methodology with recorded results which can be used to ensure compliance with regulations from relevant government agencies.

BACKGROUND OF THE INVENTION

A "below-the-hook lifting device" is a sling, hook, magnet, or vacuum device, beam or fabricated structural device that is suspended from the hook of an overhead crane or hoisting device, and used to lift an object. They are also sometimes referred to as overhead lifting devices. Under current standards for the design and manufacture of "below-the-hook lifting devices," mandatory load testing is not required of the manufacturer. On the other hand, regulatory agencies such as OSHA in the United States, often demand testing and the burden of such testing often falls on the user to provide certification that the lifting device has been load tested prior to use. Failure to comply with testing can result in large fines being levied on the user.

Many manufactures of "below-the-hook lifting devices" (hereinafter "lifting device," "test device" or "test lift device") produce such lift devices in batches of several hundred in a single production run. In order to provide testing certification for end-user purchasers, the manufacturer may choose to load test random numbers of lift devices produced in a single production run. This practice does not guarantee that all produced lift devices satisfy the regulatory standards, and it is preferable that every lift device produced be load tested before delivery to a customer. Unfortunately, such a task has to date been prohibitably expensive.

For the above reasons, what is needed is a load test system which can be used by a manufacturer to test every lift device produced in a cost effective way, and with the ability to provide accurate certification to an end-user purchaser that the lift device purchased has been tested and satisfies regulatory standards.

SUMMARY OF THE INVENTION

The invention is a load test system for lift devices which includes a test bed frame. The test bed frame extends horizontally along a first axis. Two rolling beams are movably mounted securely in the test bed frame for being moved to desired positions along the first axis within the test bed frame and, in a specific aspect, the rolling beams can be locked into position therein. The rolling beams include plural attachment locations for attaching a test lift device thereto. A hydraulic power station is spaced from the test bed frame along a second axis perpendicular to the first axis. The hydraulic power station includes a connecting line connected to a hydraulic cylinder in the power station at one end, and connectable to a test lift device at another end for applying a load to the test lift device when the test lift device is attached to the test bed frame and to the hydraulic power stations hydraulic cylinder. Beam members serve to connect the hydraulic power station and the test bed frame to form a rigid structure.

In a specific aspect, the rigid structure is arranged to have the connecting line extend horizontally, and includes a winch and slack take up cable associated with the connecting line for taking up any slack in the connecting line when connected to a test lift device to be tested resulting from gravitational pull toward the floor of the rigid structure.

Embodiments include at least one load sensor associated with the hydraulic cylinder for measuring a load applied to the test lift device. At least one camera may be provided for visually recording a load test conducted on the test lift device.

A hardened monitoring and control station may also be provided separate from the rigid structure, and may be enclosed and hardened to protect a user conducting the test in the event of catastrophic failure and debris resulting from failure of a test lift device during a test. Recording devices and display devices may also be located in the monitoring and control station to record data picked up by the load sensors resulting from the test, as well as to visually record the test through use of the camera, and to display the data and images.

These and other advantages and features that characterize the invention are set forth in the claims annexed hereto and forming a further part hereof. However, for a better understanding of the invention, and of the advantages and objectives attained through its use, reference should be made to the Drawings, and to the accompanying descriptive matter, in which there are described exemplary embodiments of the invention.

BRIEF DESCRIPTION OF THE DRAWINGS

FIG. 1 shows in perspective view a load test system in accordance with the invention with some components removed for the sake of clarity.

FIG. 2 is a partial view of a rolling beam viewed from the front as mounted on the test bed frame.

FIG. 3 is a partial view of a rolling beam viewed from the rear as mounted on the test bed frame.

DETAILED DESCRIPTION OF THE INVENTION

Figure 4:
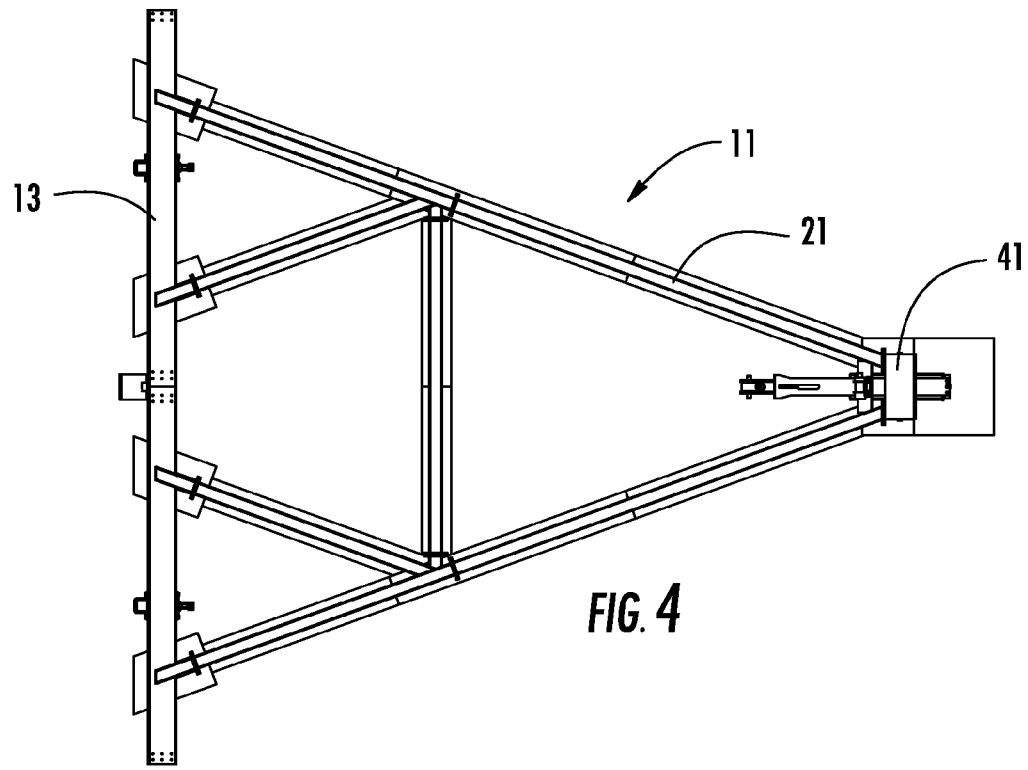
FIG. 4 is a top plan view of the load test system rigid structure.

In one respect, embodiments consistent with the invention may capitalize on a load test system that can test a wide variety of shapes and sizes, based in part upon a rolling beam feature, and the size of the load test system which provides numerous anchoring locations so that the test lift device can be properly evaluated and tested under conditions substantially approximating actual field conditions.

FIG. 1 illustrates in perspective view a load test system 11 in accordance with the invention, with some of the components thereof not shown for the sake of clarity. A test bed frame 13 extends horizontally along a first axis and includes rolling beams 15 which typically have a number of connection points spaced equally along the vertical axis of the beams 15 for attachment of pad eyes 17. The beams 15 can roll back and forth along the test bed frame 13 as more clearly shown in FIGS. 2 and 3 through the means of rollers 101. Securing tabs 19 on the rear side of the test bed frame 13 serve to secure the rolling beams 15 on the test bed frame 13 when undergoing a load test and resulting in forces applied in the direction of the arrow 18 shown in FIGS. 2 and 3. Optionally, rolling beams 15 can be locked in place to prevent further horizontal movement.

A hydraulic power station 41 is provided along an axis perpendicular to the test bed frame 13 and includes a hydraulic ram or cylinder with a connecting line as shown and described hereafter, for applying a load on a test lift device secured to the test bed frame 13, for example, at the pad eyes 17.

The hydraulic power station 41 also includes a winch arrangement, as described hereafter, for taking up slack on a horizontally extending connecting line connected to a test lift device. The winch arrangement is powered by hydraulic fluid passing through hydraulic winch lines 49 and 51. Hydraulic fluid is also passed through hydraulic pull and push lines 43 and 45 for powering the hydraulic ram/cylinder. The pressurized hydraulic fluid is provided by hydraulic pumping unit 47 shown separate from the hydraulic power station 41.

Optionally, a hydraulic pressure meter (not shown) can be connected to the lines 43 and 45 and housed in the monitoring and control station. The reading of the pressure from the meter can serve as an indirect indicator of a load placed on a test lift device.

As may be appreciated, the hydraulic power station 41 may also include a load cell connected to the hydraulic ram to transmit data through wire 55 to a load cell read out 57. One or more cameras 53 may also be positioned for recording a test and may be connected to a display device 59 within a monitoring and control station, which is separate and distinct from the location where the tests are conducted.

The hydraulic power station 41 is connected to the test bed frame 13 through means of upper beam members 21 and lower beam members 31. The lower beam members 31 are preferably recessed (such as in a floor) to allow test lift devices to be passed into the rigid structure, which is made up of the connection of the test bed frame 13 beam members 21 and 31 and hydraulic power station 41.

With respect to the monitoring and control station, although not shown in an enclosed area, the monitoring and control station is an optionally separate room with a harden enclosure (not shown) to protect the operator against catastrophic failure and debris resulting from such failure when a load test is conducted on a test lift device. A display and load cell read out may be connected to recording devices as part of operating control box 61 to provide a permanent visual record and read out of a load applied during a test, and the operation of the test lift device in response to such load during the test being conducted.

Figure 5:
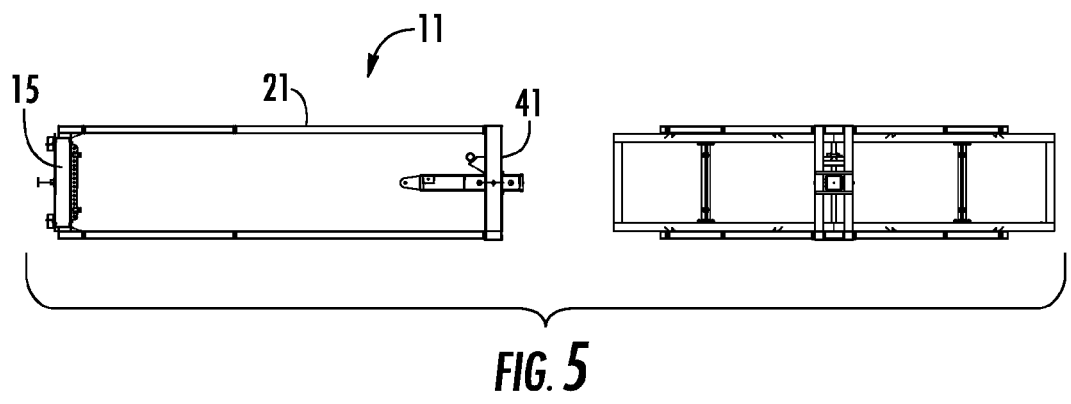
FIG. 5 is a side view of the load test system rigid structure.

For ease of further understanding, it is noted that FIGS. 4 and 5 illustrate in top-plan view and side view of the rigid structure of the load test system 11 of the invention.

Figure 6:
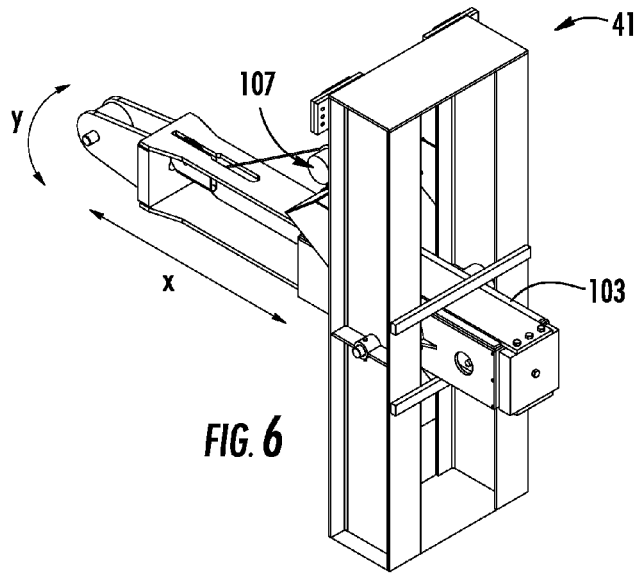
FIG. 6 is a perspective view of the hydraulic power station.
Figure 7:
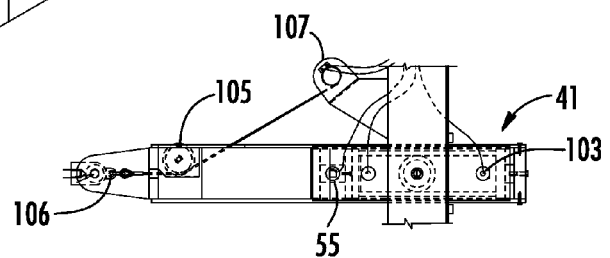
FIG. 7 is a side view in partial cross section of the hydraulic power station.

The hydraulic ram or cylinder arrangement of the hydraulic power station 41 is shown in greater detail in FIGS. 6-7. As shown in FIGS. 6-7, a pulley 105 with a winch 107 arrangement can be connected to the connecting line 106 for the test lift device to pull on the connecting line 106. The connecting line 106 may be a chain in one exemplary embodiment. Slack in the connecting line 106 is optionally taken up by pulling the connecting line along line X (shown in FIG. 6) to bring it into a taught horizontally extending state upon actuation of hydraulic ram 103. The ram 103 includes a hydraulic cylinder, and no movement is wasted by taking up slack along direction X. As will be more readily appreciated, the hydraulic power station with the hydraulic ram 103 can also pivot about a pivot point along the arrow Y as shown in FIG. 6, depending on the lift device being tested.

Figure 8:
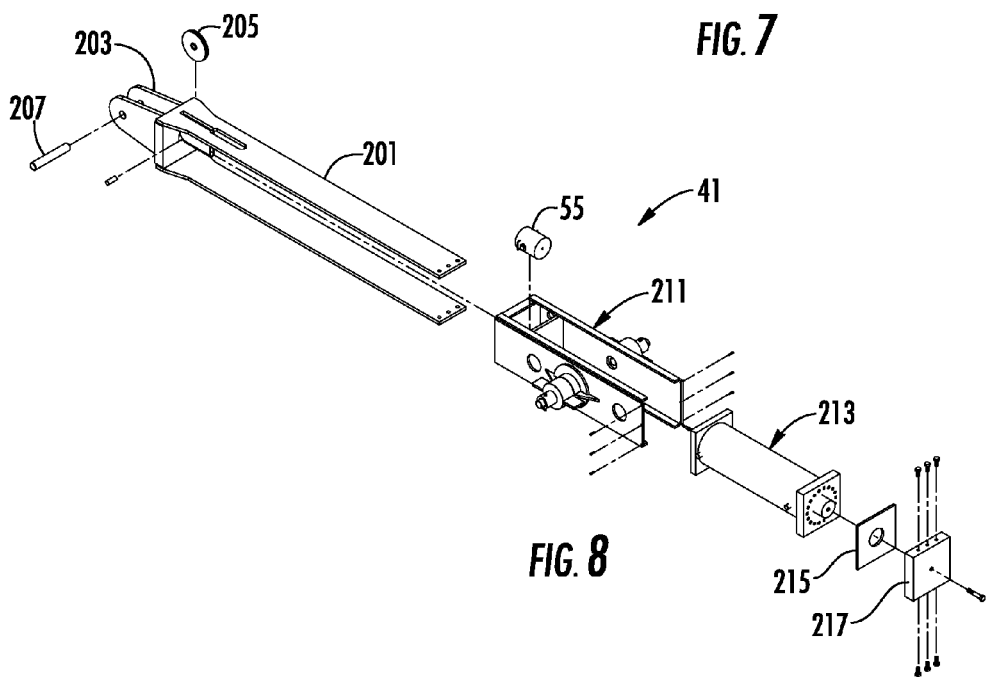
FIG. 8 is a view in disassembled form of a portion of the hydraulic power station.

The components making up the hydraulic ram 103 are further shown in FIG. 8 and include an outside cylinder assembly 201 which fits over an inside cylinder assembly 211. The outside cylinder assembly includes a cable pulley 205 assembled on a cable pulley assembly 203 through pin 207. A load cell 55 is located on the inside cylinder assembly in association with hydraulic cylinder 213, which when actuated through hydraulic fluid pressure, moves rearwardly along the direction of arrow X of FIG. 6 towards a cylinder endplate 215 and backstop block 217.

Figure 9:
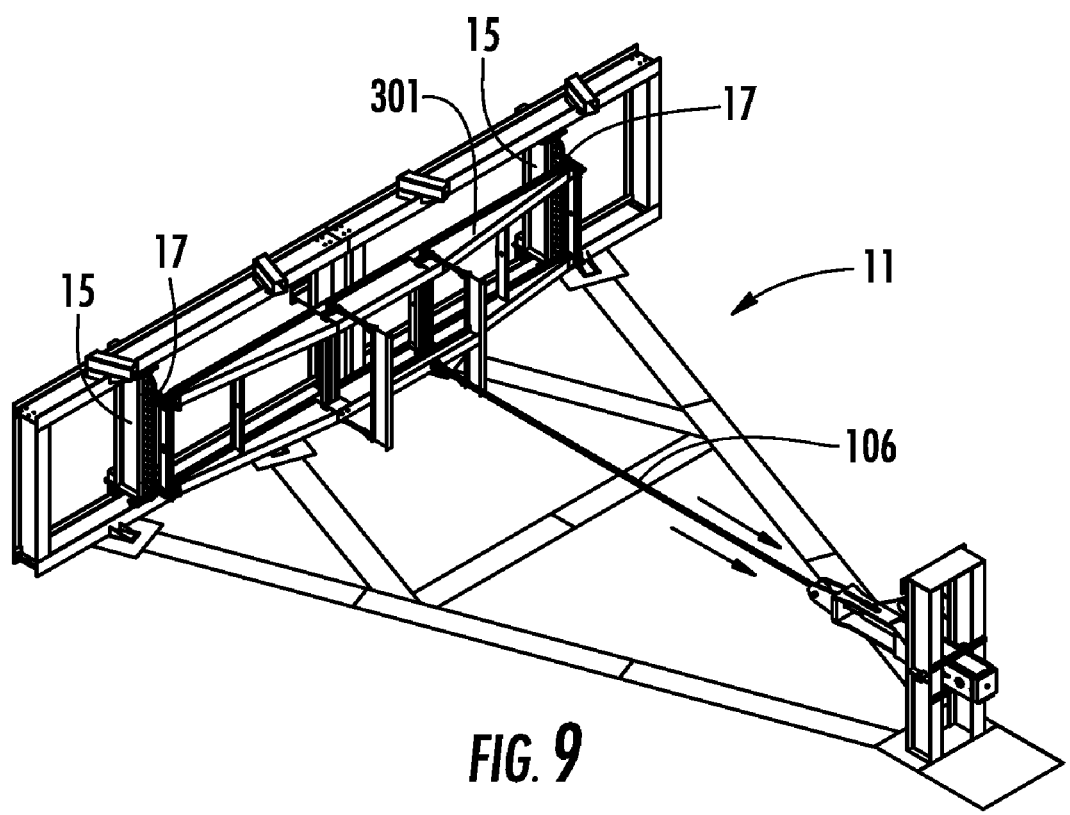
FIG. 9 is a partial perspective view of the load test system shown testing a forklift spreader.
Figure 10:
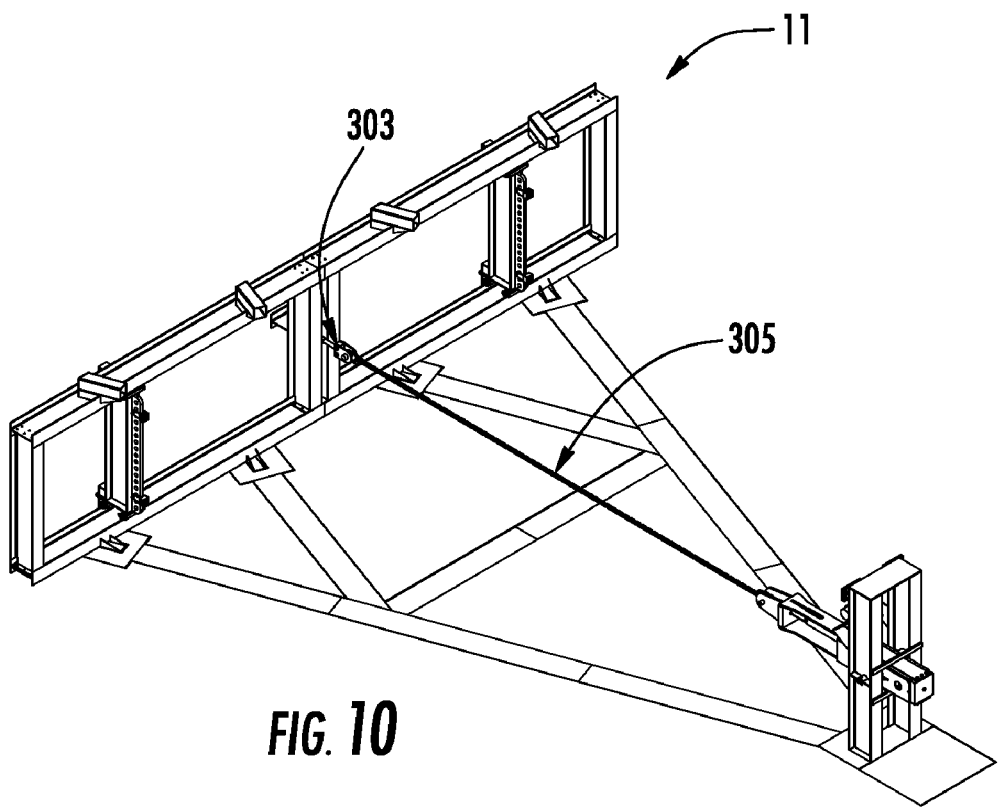
FIG. 10 is a partial perspective view of the load test system shown testing a straight piece of chain.
Figure 11:
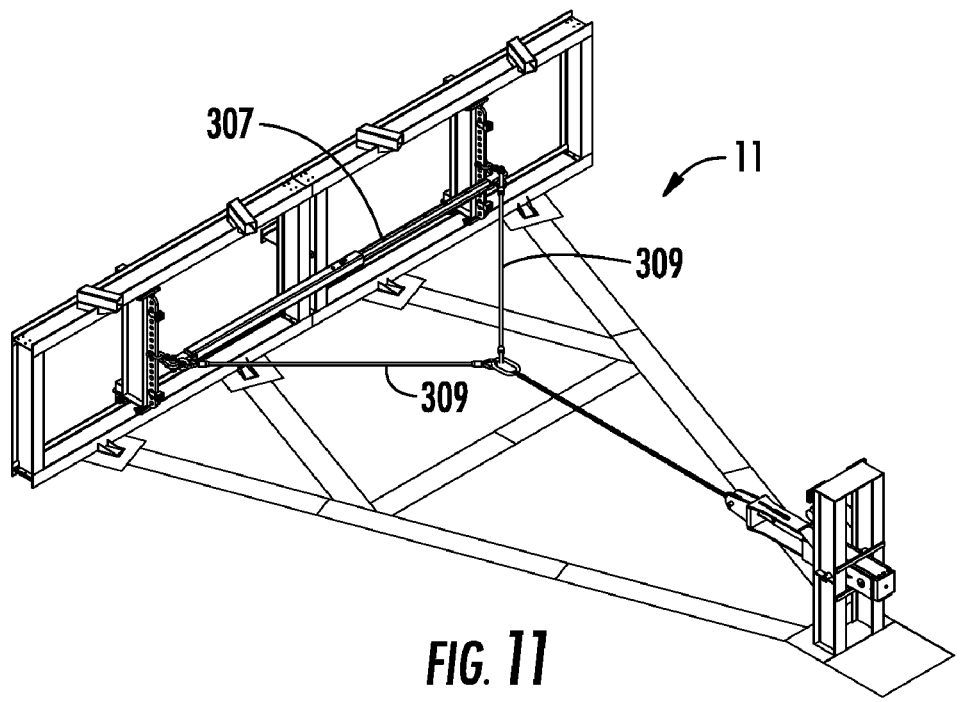
FIG. 11 is a partial perspective view of the load test system shown testing a telescopic spreader.

FIGS. 9-11 illustrate various tests being conducted with the load test system 11 of the invention. In the case of FIG. 9, a forklift spreader 301 is attached to the rolling beams 15 at the pads 17, and with the rolling beams 15 being placed at selected locations. The connecting line 106, preferably a cable, is connected to the forklift spreader 301. A load is applied along the direction of the arrow shown in association with the connecting line 106.

FIG. 10 illustrates a load test system 11 conducting a test on a chain 305 which replaces connecting line 106. The chain 305 is put under stress by attachment to a central support beam at an anchor point 303 having a clevis adaptor. In the case of FIGS. 9 and 10 as well as FIG. 11, the top structure, i.e., beam members 21, of the test load system has been removed for clarity of understanding.

FIG. 11 illustrates a load test on a telescopic spreader 307. Shackles connect the spreader 307 to the rolling beams 15 of the test bed frame 13. Cables 309 connect the spreader to the connecting line 106.

Figure 12:
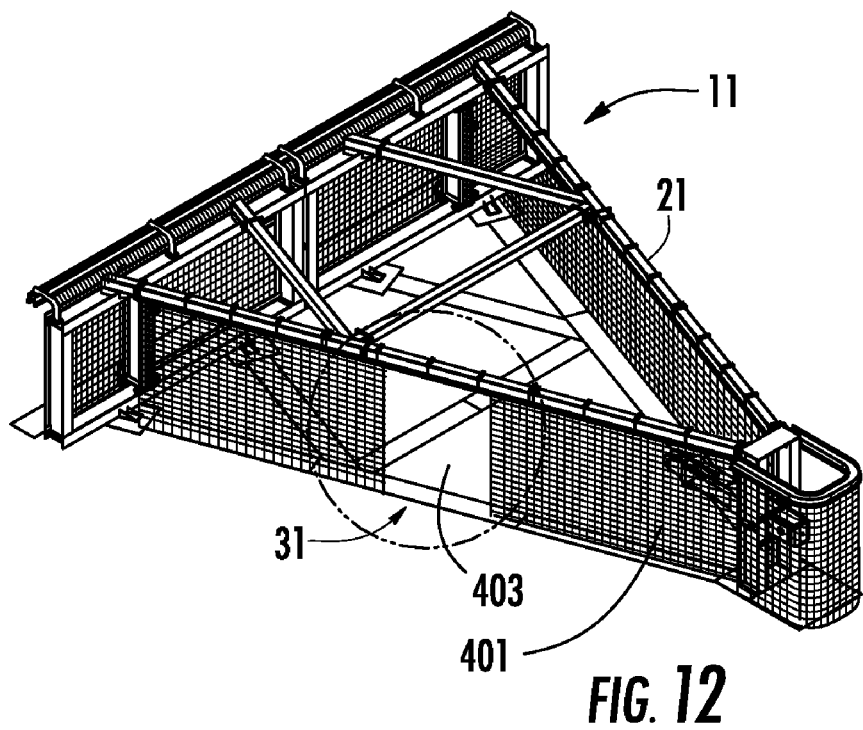
FIG. 12 is a partial perspective view of the load test system, shown with a mesh wire assembled thereon.
Figure 13:
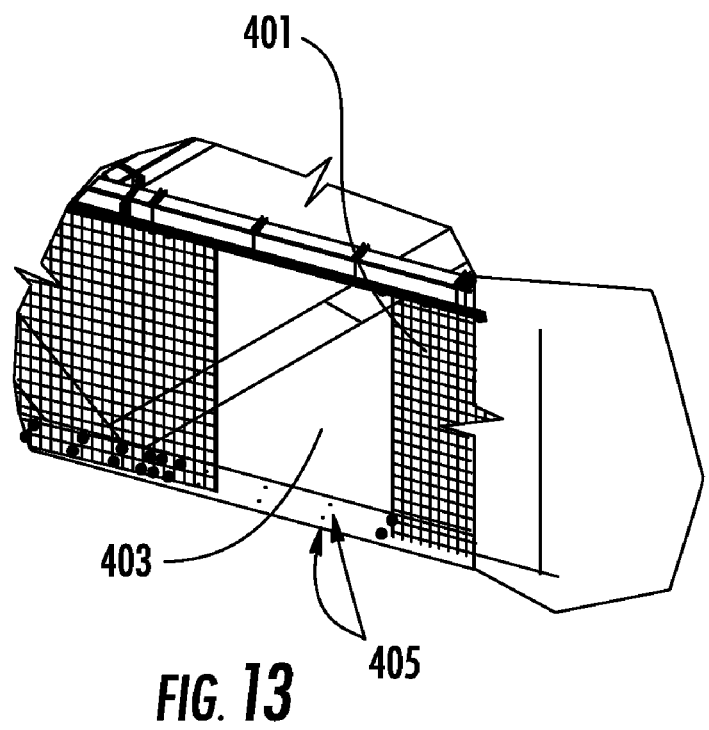
FIG. 13 is a perspective view of the circled portion of FIG. 12, showing how the wire mesh slides open and closed, and is attached to the rigid structure.

FIGS. 12 and 13, respectively, illustrate in perspective view a barrier mesh 401 which can be attached around the load test system 11 to prevent debris resulting from a test failure from flying out of the rigid structure. The mesh 401 can be arranged in two substantially parallel layers as an inner and outer layer of mesh. The mesh 401 is slideably mounted in connection with the beam members 21 and 31 so as to allow an opening 403 resulting from sliding motion. Once the mesh 401 is closed, it can be secured through attachment holes 405 to provide a more rigid structure and protection for those around the load test system 11.

It will be appreciated that test load capabilities for the system can be engineered in a conventional manner. For example, a system capable of applying a load of 750,000 lb may be engineered for use with loads of up to 600,000 lb. for periods of about 3 to about 5 minutes on a test lift device. The extra capacity provides a margin of safety. Further, as will be appreciated, through the use of appropriate jig arrangements, such test loads can be effectively multiplied by factors of 3 to 5 times the design tolerances.

While the present invention has been illustrated by a description of various embodiments and while these embodiments have been described in considerable detail, it is not the intention of the Applicants to restrict, or any way limit the scope of the appended claims to such detail. The invention in its broader aspects is therefore not limited to the specific details, representative apparatus and method, an illustrative example shown and described. According, departures may be made from such details without departing from the spirit or scope of Applicants' general inventive concept.

What is claimed is:

1. A load test system, comprising:
    a test bed frame extending horizontally along a first axis, said test bed frame further comprising at least two rolling beams movably mounted securely in said test bed frame for being moved to desired positions along said first axis within said test bed frame, said rolling beams having plural attachment locations for attaching a test device thereto;
    a hydraulic power station located spaced from said test bed frame along a second axis perpendicular to said first axis, said hydraulic power station having a connecting line connected to a hydraulic cylinder in the hydraulic power station at one end, and connectable to a test device at another end for applying a load to a test device when a test device is attached to said test bed frame, and to said hydraulic power station, through actuation of said hydraulic cylinder; and
    beam members connecting said hydraulic power station and said test bed frame to form a rigid structure, and said rigid structure being arranged to have said connecting line extend horizontally, and further comprising a slack take up mechanism for taking up any slack in said connecting line when connected to a test device to be tested.

2. The load test system of claim 1 wherein said at least two rolling beams comprise a locking mechanism for locking of said beams in said position therein.

3. The load test system of claim 1, wherein said slack take up mechanism comprises a winch and cable.

4. The load test system of claim 3, wherein said connecting line is a chain.

5. The load test system of claim 1, further comprising a wire mesh screen slidably mounted on said rigid structure for enclosing said rigid structure when a load test is being conducted.

6. The load test system of claim 1, further comprising at least one load sensor associated with said hydraulic cylinder for measuring a load applied to a test device.

7. The load test system of claim 6, further comprising a monitoring and control station separate from said rigid structure for controlling operation of said load test system.

8. The load test system of claim 1, further comprising at least one camera for visually recording a load test conducted on a test device.

9. The load test system of claim 8, wherein said at least one camera comprises a plurality of cameras disposed at different locations relative to a test device to be tested for visually recording a load test on a test device from different angles.

10. The load test system of claim 1, further comprising pad eyes on said rolling beams extending along a third axis perpendicular to said first axis and to said second axis, and further comprising securing tabs for preventing said rolling beams from being pulled from said test bed frame during a test.

11. The load test system of claim 1, wherein said beam members making up a bottom portion of said rigid structure are recessed into a floor of said load test system.

12. The load test system of claim 1, further comprising a hydraulic pumping unit connected to said hydraulic power station for providing hydraulic pressure to power said hydraulic power station.

13. The load test unit of claim 12, further comprising a hydraulic pressure meter connected to said hydraulic pumping unit for monitoring hydraulic pressure during a test as an indication of a test load being applied to a test device.

14. The load test system of claim 1, further comprising a monitoring and control station separate from said rigid structure for controlling operation of said load test system.

15. A load test system, comprising:
    a test bed frame extending horizontally along a first axis, said test bed frame further comprising at least two rolling beams movably mounted securely in said test bed frame for being moved to desired positions along said first axis within said test bed frame, said rolling beams having plural attachment locations for attaching a test device thereto;
    a hydraulic power station located spaced from said test bed frame along a second axis perpendicular to said first axis, said hydraulic power station having a connecting line connected to a hydraulic cylinder in the hydraulic power station at one end, and connectable to a test device at another end for applying a load to a test device when a test device is attached to said test bed frame and to said hydraulic power station, through activation of said hydraulic cylinder;
    beam members connecting said hydraulic power station and said test bed frame to form a rigid structure extending in a horizontal plane between said test bed frame and said hydraulic power station;
    at least one load sensor associated with said hydraulic cylinder for measuring a load applied to a test device, and at least one camera for visually recording a load test conducted on a test device;
    said connecting line extending horizontally, and said load test system further comprising a winch and slack take up cable for taking up any slack in said connecting line when connected to a test device to be tested; and
    a wire mesh screen slidably mounted on said rigid structure for enclosing said rigid structure when a load test is being conducted.

16. The load test system of claim 15, wherein said at least two rolling beams comprise a locking mechanism for locking of said beams in said position therein.

17. The load test system of claim 15, wherein said beam members making up a bottom portion of said rigid structure are recessed into a floor of said load test system.

18. The load test system of claim 15, further comprising a hydraulic pumping unit connected to said hydraulic power station for providing hydraulic pressure to power said hydraulic power station.

19. The load test system of claim 18, further comprising a hydraulic pressure meter connected to said hydraulic pumping unit for monitoring hydraulic pressure being provided during a test as an indicator of a test load being applied to a test device.

20. The load test system of claim 15, further comprising a monitoring and control station separate from said rigid structure for controlling operation of said load test system.

21. The load test system of claim 20, wherein said monitoring and control station further comprises a hardened enclosure, and has at least one display device and at least one recording device connected to said at least one camera for visually observing and recording a test, and said at least one load gauge connected to said at least one recording device and to said at least one load sensor for observing and recording a load test.

22. The load test system of claim 21, further comprising a plurality of cameras and a plurality of load sensors connected respectively to said at least one recording device, to said at least one display device and to said at least one load gauge.

23. A load test system, comprising:
- a test bed frame extending horizontally along a first axis, said test bed frame further comprising at least two rolling beams movably mounted securely in said test bed frame for being moved to desired positions along said first axis within said test bed frame, said rolling beams having plural attachment locations for attaching a test device thereto, and being capable of being locked in place at different locations on the test bed frame along said first axis;
- a hydraulic power station located spaced from said test bed frame along a second axis perpendicular to said first axis, said hydraulic power station having a connecting line connected to a hydraulic cylinder in the hydraulic power station at one end, and connectable to a test device at another end for applying a load to a test device when a test device is attached to said test bed frame, and to said hydraulic power station, through actuation of said hydraulic cylinder; and
- beam members connecting said hydraulic power station and said test bed frame to form a rigid structure.

* * * * *